United States Patent
Luo et al.

(10) Patent No.: US 9,872,880 B2
(45) Date of Patent: Jan. 23, 2018

(54) NATURAL HERBAL COMPOSITIONS FOR RAPID REMOVAL OF METABOLIC TOXINS IN THE BODY

(71) Applicant: SICHUAN SHANZE BIOTECH CO., LTD., Sichuan Province (CN)

(72) Inventors: MingFeng Luo, Sichuan Province (CN); YuChan Zhong, Sichuan Province (CN); Hong Zhang, Sichuan Province (CN); GaiLi Li, Sichuan Province (CN)

(73) Assignee: SICHUAN SHANZE BIOTECH CO., LTD., Chengdu (CN)

( * ) Notice: Subject to any disclaimer, the term of this patent is extended or adjusted under 35 U.S.C. 154(b) by 256 days.

(21) Appl. No.: 14/907,262

(22) PCT Filed: May 13, 2014

(86) PCT No.: PCT/CN2014/077365
§ 371 (c)(1),
(2) Date: Jan. 22, 2016

(87) PCT Pub. No.: WO2015/010498
PCT Pub. Date: Jan. 29, 2015

(65) Prior Publication Data
US 2016/0175374 A1    Jun. 23, 2016

(30) Foreign Application Priority Data

Jul. 23, 2013 (CN) .......................... 2013 1 0308438

(51) Int. Cl.

| | | |
|---|---|---|
| A61K 36/00 | (2006.01) | |
| A61K 36/886 | (2006.01) | |
| A61K 36/23 | (2006.01) | |
| A61K 36/232 | (2006.01) | |
| A61K 36/284 | (2006.01) | |
| A61K 36/288 | (2006.01) | |
| A61K 36/38 | (2006.01) | |
| A61K 36/484 | (2006.01) | |
| A61K 36/54 | (2006.01) | |
| A61K 36/704 | (2006.01) | |
| A61K 36/708 | (2006.01) | |
| A61K 36/258 | (2006.01) | |

(52) U.S. Cl.
CPC ............ *A61K 36/886* (2013.01); *A61K 36/23* (2013.01); *A61K 36/232* (2013.01); *A61K 36/258* (2013.01); *A61K 36/284* (2013.01); *A61K 36/288* (2013.01); *A61K 36/38* (2013.01); *A61K 36/484* (2013.01); *A61K 36/54* (2013.01); *A61K 36/704* (2013.01); *A61K 36/708* (2013.01)

(58) Field of Classification Search
CPC ....................................................... A61K 36/00
USPC .......................................................... 424/725
See application file for complete search history.

(56) References Cited

U.S. PATENT DOCUMENTS

2010/0119653 A1* 5/2010 Hall ..................... C12Q 1/6883
426/62

* cited by examiner

*Primary Examiner* — Michael V Meller
(74) *Attorney, Agent, or Firm* — WPAT, P.C., INTELLECTUAL PROPERTY ATTORNEYS; Anthony King

(57) ABSTRACT

The present invention provides a natural herbal composition for rapid removal of metabolic toxins in the body, to solve the problems of existing herbal compositions such as slow efficacy for such symptoms as constipation, bad breath, acnes caused by accumulated toxins in the body, side and toxic effects, etc. The natural herbal composition comprises the following ingredients (by mass): mangosteen extract, aloe extract, hot water extract of mixture of dandelion 1-30, *Angelica sinensis* 1-20, *Polygonum multiflorum* 1-30, *Cinnamomum cassia* 3-16, rheum officinale 4-20, *Glycyrrhiza uralensis* 3-10, *Panax notoginseng* 3-10, *Atractylodes macrocephala* 5-15, wherein the mass ratio of mangosteen fruit extract to aloe extract is 3:1-5, and the mass ratio of mangosteen and aloe extracts to the hot water extract is 2:1-5.

1 Claim, No Drawings

NATURAL HERBAL COMPOSITIONS FOR RAPID REMOVAL OF METABOLIC TOXINS IN THE BODY

CROSS-REFERENCE TO RELATED APPLICATIONS

This application is the National Stage Application of PCT Patent Application No. PCT/CN2014/077365, filed on May 13, 2014, with a priority date of Jul. 23, 2013 which is based on a China Patent Application number 201310308438.1, now China Patent No. ZL 2013 1 0305438.1, all which are hereby incorporated by reference in their entireties.

Although incorporated by reference in its entirety, no arguments or disclaimers made in the parent application apply to this National Stage Application. Any disclaimer that may have occurred during the prosecution of the above-referenced application(s) is hereby expressly rescinded.

FIELD OF THE DISCLOSURE

The present disclosure relates to a composition with the compound crude drug extract as active ingredient used for preventing constipation, bad breath, acnes caused by accumulation of metabolic toxins, in particular, to a composition made with active ingredients of compound crude drug extracts including mangosteen, aloe vera, dandelion, *Angelica sinensis*, *Polygonum multiflorum*, *Cinnamomum cassia*, *rheum officinale*, *Glycyrrhiza uralensis*, *Panax notoginseng* and *Atractylodes macrocephala* having the efficacy of antioxidant effect, reducing blood viscosity and improving the symptoms of constipation. It is used for preventing constipation, bad breath and acnes caused by excessive metabolic toxins in the body.

BACKGROUND OF THE DISCLOSURE

In modern society, with the accelerated pace of life, irregular life, excessive stress, lack of exercise, poor body metabolism, and environmental pollution, much harmful toxins are accumulated in human body. These toxins are mainly from wastes and environmental pollution after the absorption and metabolism of foods. If these toxins can be removed out of the body, people can maintain a healthy state; and if unable to remove timely, and when the accumulated in vivo toxins exceed human body's resistance, body functions will be lowered, and such symptoms as bad breath, constipation, acne, dull skin will occur, and if serious it would cause hypertension, hyperlipidemia, heart disease and kidney failure, etc. The toxic wastes and fats would be attached to the blood vessels to obstruct the blood flow, and these blocked vessels will become hardened and thickened, the heart's ability to pump blood is reduced and the burden on heart will increase, causing hypertension, blood clots, heart attack and stroke.

When the body's toxic wastes are attached to the intestinal wall, the secretion of digestive juice will be reduced gradually to lower the digestion, causing indigestion, and even gastrointestinal inflammation. When the wastes increase, the intestinal tract is blocked seriously, causing bowel problems, and even constipation. Toxins generating from wastes unable to remove out of the body in the intestines will enter the blood circulation, to induce systemic symptoms, such as acne, dull skin, and etc.

If the metabolic toxins in human body can be removed timely and effectively, it can achieve the purpose of beautifying and longevity; people in sub-health state can recover healthy, enhancing the quality of life of people in subhealth state.

At present, there are a number of products that can be used for removing the body toxins, but most of them have single effect and large side effects. Some people use laxatives to relieve their chronic constipation, to remove metabolic toxins from the body, but this may make the problem worse. The laxatives may stimulate the intestinal wall, enhance intestinal peristalsis, thereby speeding up the discharge of intestinal wastes; but a long-term use of laxatives can cause wall thinning, reduce intestinal digestion and absorption capacity, affecting the normal digestive functions of the intestinal tracts, and even dehydrating the body if severe.

Currently, there are patents related to compositions that can reduce accumulation of metabolic toxins in the intestine by increasing the frequency of bowel movements and enhancing the fluid secretion in the intestines to accelerate the excretion of feces, for example, Chinese Patent CN 101987167 A. It relates to an herbal composition, which can remove intestinal metabolic toxins by increasing the fluid secretion in the intestines and accelerating the intestinal peristalsis. Although this method can quickly remove the intestinal metabolic toxins to a certain extent, it has diarrhea and other side effects, and if used for a long time, it may lead to enteritis and dehydration. The invention relates to a powder, not easy to use or preserve.

BRIEF SUMMARY OF THE DISCLOSURE

The object of the present invention is to provide a natural herbal composition that can quickly remove the metabolic toxins in the body for preventing constipation, bad breath, acnes caused by accumulation of metabolic toxins. It is easy to use and preserve, with fewer side effects.

The invention is achieved through the following technical solutions:

A natural herbal composition for rapid removal of metabolic toxins in the body, comprising the following ingredients (by mass): mangosteen extract, aloe extract, hot water extract of mixture of dandelion 1-30, *Angelica sinensis* 1-20, *Polygonum multiflorum* 1-30, *Cinnamomum cassia* 3-16, *rheum officinale* 4-20, *Glycyrrhiza uralensis* 3-10, *Panax notoginseng* 3-10, *Atractylodes macrocephala* 5-15, wherein the mass ratio of mangosteen fruit extract to aloe extract is 3:1-5, and the mass ratio of mangosteen fruit extract, aloe extract and hot water extract is 2:1-5.

The mangosteen fruit extract, aloe extract are the powder obtained through the concentration of the ethanol extract under reduced pressure and drying.

The hot water extract is powder obtained through the following procedures: firstly cut or crush the crude drugs of dandelion, *Angelica sinensis*, *Polygonum multiflorum*, *Cinnamomum cassia*, *rheum officinale*, *Glycyrrhiza uralensis*, *Panax notoginseng*, *Atractylodes macrocephala* and then mix them, add 6-10 times of water of the mixed amount of medicinal materials to boil and maintain 30 min, to get the filtrate; and then add water equal to 5-7 times of the mixed amount of medicinal materials to boil and maintain 30 min, to get the filtrate, and then combine the filtrate, concentrate and dry under reduced pressure, to get the powder.

The mangosteen fruit extract is the powder obtained from the soluble ethanol extract of mangosteen fruit after concentration and drying under reduced pressure. Specifically, crush the peel, pulp and kernel of mangosteen fruit, and through reflux extraction in 75% ethanol, to get the powder after drying under normal temperature and reduced pressure.

The aloe extract is the water-soluble alcohol extract of aloe. Specifically, cut the aloe into pieces and add 2-5 times of water to crush, then subject to ultrasonic treatment, then add 5-10 times of 75% ethanol for extraction, and finally concentrate and dry under vacuum condition at 40-60° C., to get the powder.

The mixing ratio of the mangosteen fruit extract and aloe extract is 3:1-5, and this ratio has great significance for this invention to remove toxins in the blood and improve the liver and kidney functions.

The dandelion is the whole plant of dandelion, which contains a variety of healthy nutrients such as taraxol, taraxacin, choline, organic acids, synanthrin etc., having the efficacy of diuresis, laxative, anti-bacterial anti-inflammatory, and protecting livers and gall bladders, etc. Dandelion also contains protein, fat, carbohydrates, trace elements and vitamins, with rich nutrition.

The *Angelica sinensis* is the dried roots of Umbelliferae *Angelica sinensis* (Oliv.) Diels, containing Butylidenephthalide, β-Pinene, a-Pinene, Camphene, sucrose , fructose, glucose, Vitamin A, vitamin B 12 vitamin E; 17 kinds of amino acids and over 20 kinds of inorganic elements including sodium, potassium, calcium, magnesium, etc. It has the efficacy of antithrombus, anti-inflammation, promoting blood circulation, anti-anoxia, enhancing body's immunity, beautifying and skin care, etc.

The *Polygonum multiflorum* is the dried roots of *Polygonum multiflorum* Thunb., which mainly contains anthraquinone compounds, including emodin, chrysophanol and physcion, rhein, chrysophanolanthrone. It has the efficacy of promoting bowel movement, regulating endocrine disorders, promoting the hematopoietic function, enhancing immunity, lowering blood lipids, anti-atherosclerosis, and protecting liver, etc.

The *Cinnamomum cassia* is the dry bark of Lauraceae *Cinnamomum cassia* Presl, and its main ingredients include cinnamaldehyde, cinnamyl acetate, ethylcinnamate, benzyl benzoate, benzaldehyde and coumarin, etc., having the efficacy of promoting glucose metabolism, accelerating blood circulation, relieving pains and antidiarrheic, etc. It has the efficacy of antibacterial, anti-inflammatory, antipyretic, antioxidation, lowering blood lipids, protecting liver and gall bladder, hemostasis and diarrhea, etc. Its purgative effect is caused by increased bowel movements when the sennoside in the rheum officinale is decomposed to generate chrysophanolanthrone under the action of bacterial enzymes in the intestines, which stimulate the intestinal mucosa. In addition, it can also inhibit the Na+, K+-ATP enzyme on intestinal cell membrane, hinder Na+ transport, to enhance the intestinal osmotic pressure, maintain a large amount of water, promote bowel movements and diarrhea.

The *Glycyrrhiza uralensis* is the dried roots and rhizomes of legumes *Glycyrrhiza uralensis* Fisch., *Glycyrrhiza inflata* Bat. or *Glycyrrhiza glabra* L, and its main ingredients include glycyrrhizic acid, liquiritin, glycyrrhizin, licoflavone, etc. It has the efficacy of anti-inflammatory inflammatory and anti-allergic reactions, alleviating cough, phlegm, treating sore throat and laryngitis; *Glycyrrhiza uralensis* or glycyrrhetinic acid has the function of deoxycorticosterone, having good efficacy for chronic adrenal cortex hypofunction. *Glycyrrhiza uralensis* can promote the formation and secretion of gastric mucus, extend the life of epithelial cells and has the anti-inflammatory activity, mainly used in the treatment of chronic ulcers and duodenal ulcers. The *Glycyrrhiza uralensis* flavonoids have the anti-inflammatory, antispasmodic and antacid functions.

The *Panax notoginseng* is the dry roots of Araliaceae *Panax notoginseng* (Burk.) F. H. Chen, and its main ingredients include notoginsenoside, dencichine and a variety of amino acids and trace elements. The product can shorten the bleeding and clotting time and has the function of anti-platelet aggregation and thrombolysis, showing remarkable hemostatic effect; it can promote the proliferation of multifunctional hematopoietic stem cells with the hematopoietic effect; lower the blood pressure and slow down heart rate, having the protective effect of drug-induced arrhythmia It can reduce myocardial oxygen consumption and oxygen utilization, dilate cerebral blood vessels, increase cerebral vascular flow; and also improve the humoral immune functions, showing analgesic, anti-inflammatory, anti-aging effects.

The *Atractylodes macrocephala* is the dried rhizome of Compositae *Atractylodes macrocephala* Koidz., and its main ingredients include atractylenolide, amino acids, fructose, starch, etc. It has remarkably diuretic, antibacterial, hypoglycemic, anticoagulant effects; in addttion, it can promote blood circumation and hematopoietic function.

The Mangosteen fruit extract, aloe extract and hot water extract containing dandelion, *Angelica sinensis*, *Polygonum multiflorum*, *Cinnamomum cassia*, *rheum officinale*, *Glycyrrhiza uralensis*, *Panax notoginseng*, *Atractylodes macrocephala* constitute the active ingredients of the pharmaceutical composition.

The preparation of pharmaceutical compositions requires carriers, adjuvants and diluents, etc. The said carriers, adjuvants and diluents include sorbitol, mannitol, xylitol, erythritol, maltitol, starch, gelatin, sodium alginate, calcium carbonate, sodium hydrogencarbonate, sodium carbonate, calcium phosphate, cellulose, methyl cellulose, sodium carboxymethyl cellulose, microcrystalline cellulose, aerosil, polyvinyl pyrrolidone, water, methyl hydroxybenzoate, hydroxypropyl methyl cellulose, talc, lactose, sucrose, glucose, magnesium stearate, and mineral oil, etc.

The pharmaceutical compositions can be made into powders, preparations for external application, tablets, capsules, suspensions, emulsions, syrups, aerosols and other oral preparations, topical suppositories and sterile injectable solutions according to common methods.

Specifically, when made into preparations, commonly-used filling agents, binding agents, wetting agents, disintegraing agents, surface-active agents and other diluents or excipients can be used for mixing.

Oral solid preparations include tablets, pills, powders, granules, capsules, etc. The extracts or powders can be mixed with one or more excipients, such as adding starch, calcium carbonate, sucrose, gelatin, to prepare solid preparations. In addition to simple excipient, lubricating agents such as talc, aerosil, magnesium stearate can be used. Oral liquid preparations include suspensions, oral solution, emulsions, syrups, etc. In addition to the simple diluent water and liquid paraffin, a variety of excipients such as wetting agents, sweetener agents, flavoring agents and preservatives can be used. Non-oral liquid preparations include sterile aqueous solution, non-aqueous agents, suspensions, emulsions, lyophilized formulations and suppositories. Water-insoluble solvents and suspensions can be propylene glycol, polyethylene glycol, vegetable oils like olive oil and injectable esters like ethyl oleate, etc. The suppository matrix can be polyethylene glycol, polysorbate, cocoa powder, *Acer laurinum*, gelatin and glycerin, etc.

In the present invention, the preferred dosage can be determined according to the patient's state, weight, degree of illness, dosage form, route of administration, and technicians skilled in the art can select appropriate dosage. In order to achieve the desired effect, the dosage is 0.1-100 g/kg, and preferably, 0. 1-80 g/kg, which can be administered once or several divided doses per day. The weight of the invention can be 0.1-60% of the total weight of pharmaceutical compositions.

The natural herbal composition in the invention can be used as health food for detoxifying and beautifying, which can be directly used as food according to common method, or taken with other foods or food ingredients. The mixing amount of active ingredients can be determined according to its purposes (prevention, health-care or treatment). Generally, when used in preparing foods or drinks, the invention occupies 10-80% of the total weight of food materials, preferably 25-60%.

Without special limitation, the invention can be added to all healthy foods in common senses, including meat, sausages, chocolate, biscuits, pizza, other pasta, chewing gum, ice cream and a variety of soups, beverages, tea, drinks, alcoholic beverages and compound vitamins, etc.

The present invention can achieve the following effects:

The present invention provides a natural herbal composition with multi-target effects which can quickly remove the metabolic toxins in the body. The present invention has comprehensive effect, with rapid onset and fewer side effects. It has the efficacy of quickly removing the metabolic toxins in the intestine, improving the liver and kidney function, eliminating toxins in the blood and accelerating blood circulation, etc. Using compound crude drug extracts including mangosteen, aloe vera, dandelion, *Angelica sinensis, Polygonum multiflorum, Cinnamomum cassia, rheum officinale, Glycyrrhiza uralensis, Panax notoginseng* and *Atractylodes macrocephala* as active ingredients, it has the efficacy of antioxidant effect, reducing blood viscosity and improving the symptoms of constipation. It is used for preventing constipation, bad breath and acnes caused by excessive metabolic toxins in the body. The composition can lower blood viscosity, improve microcirculation, promote the metabolism of liver and kidney and detoxification, and alleviate symptoms caused by accumulated toxins such as constipation, bad breath, acnes. Since the composition is a natural plant ingredient, it has no toxic or side effects, to ensure its safety.

The composition in the invention has been tested with model mice of constipation, demonstrating that it can alleviate symptoms caused by accumulated toxins in the body, such as constipation.

DETAILED DESCRIPTION OF THE EMBODIMENT (1) Preparation of Mangosteen Extract

Take mangosteen 1 kg, remove the carpopodium and mash the peel, pulp and kernel, and then add 10 L of 75% of ethanol for reflux extraction at the condition of 65° C., and then dry the extracting solution under reduced pressure at room temperature, to get 120 g of powder.

(2) Preparation of Aloe Extract

Take 1 kg aloe, wash clean and cut into pieces, add 4 L of water to mash, and ultrasonic treatment, then add 8 L of 75% ethanol for extraction, finally concentrate and dry it under a vacuum condition at the temperature of 55° C., to get 200 g of powder.

(3) Preparation of Hot-water Extract

Take dandelion 100 g, *Angelica sinensis* 200 g, *Polygonum multiflorum* 150 g, *Cinnamomum cassia* 300 g, *rheum officinale* 400 g, *Glycyrrhiza uralensis* 300 g, *Panax notoginseng* 300 g, *Atractylodes macrocephala* 500 g and wash them, add 24 L of water to immerse1 hour, and then heat them to boiling and maintain 30 min; add 20 L of water to the second time of drug dregs to boiling 30 min, and then concentrate the above extracting solution under reduced pressure at 80° C. to the get the hot-water extract 600 g. Under room temperature, 20 g of mangosteen extract, 40 g of aloe extract and 150 g of hot-water extract are mixed well.

Test Example 1

Acute Toxicity Test

1. Experimental Animals (1) Animal: SPF mice (2) Source: Sichuan Academy of Traditional Chinese Medicine, Experimental Animal Center (3) Reasons for selection: mice are applicable to the toxicity tests, which are widely used in the acute toxicity test. Many basic research data of SPF mice can be available, which can be used for explanation and evaluation of the test results.

(4) Age and body weight

| | | |
|---|---|---|
| Male | Age of animals when received | 4 weeks |
| | Number of animals when received | 16 mice |
| | Body weight of animals when received | 80.5-96.2 g |
| | Age of animals when administered | 5 weeks |
| | Number of animals when administered | 12 mice |
| | Body weight of animals when administered | 115-142 g |
| Female | Age of animals when received | 4 weeks |
| | Number of animals when received | 6 mice |
| | Body weight of animals when received | 79.6-95.8 g |
| | Age of animals when administered | 5 weeks |
| | Number of animals when administered | 12 mice |
| | Body weight of animals when administered | 97-121 g |

(5) The quarantine and acclimation

Animals were visually observed the appearance when receiving, and acclimated in the animal room used for test, to observe general symptoms. Those healthy and strong animals were selected for test.

2. Feeding Environment (1) Environmental conditions: Experimental animals were housed in a clean room with temperature of about 25° C., humidity of about 55%, illumination time of 12 hours (8:00 a.m.-8:00 p.m.) and illumination intensity of 140-350 Lux. Laboratory technicians should wear autoclaved overalls, scarves, masks and gloves.

(2) Feeding Monitoring: During the test, the temperature and humidity of animal feeding room were detected once every 1 hour using automatic temperature and humidity detectors, and the lighting facilities should be monitored periodically (2 months).

(3) Experimental animals were fed in stainless steel mesh feeding chamber (220 mm×410 mm×200 mm) During the acclimatization, each feeding chamber included 4 animals, and during the administration and observation period, each feeding chamber included 3 animals. During the testing, each chamber was labeled with the test number and individual animal identification card with the animal number (control group: white, test group: yellow).

(4) Feed and water

The solid feeds were sterilized by radiation sterilization method, and animals could take feeds freely. Drinking water was sterilized by an ultraviolet disinfector, and animals could drink it freely.

3. Dosing and Test Group (1) Setting of Dosing

The dose was set at 2500 mg/kg in the preliminary test and no animals were found died, so the highest dose of 2500 mg/kg was used for limit dose test, and the solvent control group was reserved.

(2) Structure of test group, concentration and dose administered

| Group | Sex | Number of Animals (n) | Animal Number | Dosing Amount (ml/kg) | Dosing Amount (mg/kg) |
|---|---|---|---|---|---|
| Control group | Female | 3 | 1-3 | 20 | 0 |
| | Male | 3 | 4-6 | 20 | 0 |
| | Female | 3 | 7-9 | 20 | 0 |
| | Male | 3 | 10-12 | 20 | 0 |
| Test group | Female | 3 | 13-15 | 20 | 2500 |
| | Male | 3 | 16-18 | 20 | 2500 |
| | Female | 3 | 19-21 | 20 | 2500 |
| | Male | 3 | 22-24 | 20 | 2500 |

(3) Grouping and Identification of Animals

Animal grouping was made as follows: firstly, the domesticated experimental animals were weighed, and grouped at an interval of weight of 5 g, and then 12 male and 12 female animals close to the mean weight were assigned randomly to each group. Animals were identified by fur pigment labeling method and individual identification card labeling method.

4. Experimental Procedures (1) Preparation of drug solution: Prior to administration, saline for injection was used as the solvent, to prepare the test plant extract to 2500 mg/20 ml/kg. In the control group, blank saline was used.

(2) Route of administration and method: One day prior to administration, experimental animals were fasted overnight. Animals were forcibly administered drug using an injector with the probe for oral administration.

(3) Frequency and time interval of administration: in the morning every day, once a day.

(4) Calculation of dosage: The dosage was calculated by the body weight of animals weighed on the day of administration.

5. Observation and Examination Items (1) General symptoms and death of animals: On the day of administration, the general symptoms and death of animals were observed 1-6 hours after drug administration; and on the day 2 to day 15, the general symptoms and death of animals were observed every day.

(2) The experimental animals were weighed once every three days.

(3) 15 days later, all surviving animals were anatomized, bled to death, to observe the condition of viscera by the naked eye.

6. The statistical analysis of results was performed in accordance with common medical statistical techniques and methods.

7. Results

During the test, no abnormal symptoms were observed in animals in the test group. On the days 1, 3, 6, 9, 12, 15 after drug administration, the normal body weight increase was observed in all experimental animals. Dead animals were observed in the control group and the test group during the test. The LD50 of the test substance in the invention was higher than 2500 mg/kg in male and female animals. After dissection, no visible abnormal organic changes were found in all animals in the test group.

Test Example 2

Therapeutical effect of herbal composition in the invention on the constipation models of mice (1) Modeling of experimental animals:

In the test, oral diphenoxylate was used to construct constipation models of mice.

Healthy male mice were selected (body weight 22-30 g) to construct models using 10 mg/kg BW compound diphenoxylate.

(2) Preparation of drug solution: Prior to administration, the saline for injection was used as solvent, to prepare the test plant extract into aqueous solutions at 1500 mg/20 ml /kg.

(3) Preparation of ink: Acacia 100 g and water 800 ml were added to boil until the solution was clear, then activated carbon 50 g was added to boil three times, added water to constant volume 1,000 ml, and finally preserved at 4° C.

(4) Animal grouping and drug administration: 60 male mice were selected and randomly divided into blank group, model group, test group, 20 animals each group. Animals in the model group and test group were administered 10 mg/kg BW compound diphenoxylate, and animals in the blank group were administered the same volume of saline.

(5) Test Method:

During experiment, mice in the blank group and model group were given 20 ml/kg BW ink, and the mice in the test group were given appropriate amount of mixture of extract and ink, once every day, 8 days in succession. Each mouse was fed individually, free diet during the experimental period. The time for the first defecation of dark stool, the stool grains and weight within 5 hours for each mouse were observed and recorded; and at the end of observation, stools were dried to constant weight at 100° C., and the moisture content of stools was calculated. The statistical results were shown in the table below:

| Group | Number of animals | Time of first defecation of dark stool | Number of stool grains within 5 h | Moisture content of stools |
|---|---|---|---|---|
| Blank group | 20 | 65.6 ± 10.1** | 15.5 ± 2.8** | 57.2 ± 3.4** |
| Model group | 20 | 120 ± 9.7 | 7.7 ± 3.0 | 44.8 ± 2.3 |
| Test group | 20 | 100.8 ± 8.5* | 13.2 ± 4.8* | 50.9 ± 3.0** |

Remark:
$p^{**} < 0.01$,
$p^{*} < 0.05$.

(6) Compared with the blank group, the time for first defecation of dark stool, number of stool grains within 5 h and the moisture content of stools in the model group had significant differences ($p<0.01$), showing that the constipation models of mice were successfully constructed. Compared with the model group, the time for first defecation of dark stool, number of stool grains within 5 h had significant difference (($p<0.05$) and the moisture content of stools had extremely significant difference, showing that the composition in the invention could effectively improve the quality of stools and relieve the symptoms of constipation in the constipation models of mice.

Preparation of Preparations: Example 1 Preparation of Pharmaceutical Preparations (1) Preparation of Powder

| | |
|---|---|
| The mixture of the natural herbal extract composition in the invention | 20 g |
| Lactose | 15 g |

The powder was prepared by mixing all above components, and filled in the airtight bags.

(2) Preparation of Tablets

| | |
|---|---|
| The mixture of the natural herbal extract composition in the invention | 20 g |
| Corn starch | 20 g |
| Lactose | 10 g |
| Magnesium stearate | 0.1 g |

The tablet was prepared by mixing all above components according to the routine preparation method.

(3) Preparation of Capsules

| | |
|---|---|
| The mixture of the natural herbal extract composition in the invention | 20 g |
| Corn starch | 20 g |
| Lactose | 10 g |
| Magnesium stearate | 0.1 g |

The capsule was prepared by mixing all above components according to the routine preparation method, and filled in the gelatin capsules.

Preparation of Preparations: Example 2 Preparation of Foods (1) Preparation of Flour-made Foods Add the mixture of the natural herbal extract composition in the invention to the wheat flour at a ratio of 0.5-3% (by weight), and make them into breads, cakes, cookies, to alleviate the symptoms caused by accumulated toxins in the body.

(2) Preparation of Diary Products

Add the mixture of the natural herbal extract composition in the invention to the diary products such as butter, ice cream at a ratio of 3-8% (by weight), and make them into healthy diary products, to alleviate the symptoms caused by accumulated toxins in the body.

Preparation of Preparations: Example 3 Preparation of Beverages (1) Preparation of Inflatable Carbonated Drinks Mix sugar (5-10%), citric acid (0.05-0.3%), caramel (0.005-0.02%) and vitamin C (0.1-1%), and add purified water (79-94%) to make syrup. Sterilize the syrup prepared 20-180 seconds at 85-98° C., and then mix with cooling water at a ratio of 1:4, finally add 3-5% of a mixture of herbal extracts, fill the carbon dioxide, to prepare the inflatable carbonated drinks containing the mixture of herbal extracts of the invention.

(2) Preparation of Health Drink

Mix the sugar (0.5%), oligosaccharide (2%), acidic fructose (5%), salt (0.7%), water (75%) and the mixture of herbal extracts well, sterilize and package them in bottles, to prepare into health drinks.

Human Trials

A total of 24 persons having such symptoms as bad breath, constipation, mouth sores, dark complexion and dry and rough skin participated in the trials. The test product form is capsule. All participating persons took capsules made by the composition in the invention, 2 days later, the associated symptoms were improved in 48 persons; 1 week later, associated symptoms were improved in 167 persons; and 2 weeks later, associated symptoms were improved in 232 persons. 8 persons had no apparent effect after taking the drug. Overall, the effective rate of the product was 96.7%.

What is claimed is:

1. A tablet or capsule for rapid removal of metabolic toxins in the body consisting essentially of therapeutically effective amounts of mangosteen extract, aloe extract, dandelion extract, *Angelica sinensis* extract, *Polygonum multiflorum* extract, *Cinnamomum cassia* extract, *rheum officinale* extract, *Glycyrrhiza uralensis* extract, *Panax notoginseng* extract, and *Atractylodes macrocephala* extract.

* * * * *